United States Patent [19]

Yamauchi et al.

[11] Patent Number: 4,847,390

[45] Date of Patent: Jul. 11, 1989

[54] CYCLOPENTANE DERIVATIVES

[75] Inventors: Takayoshi Yamauchi; Kaneaki Hattori; Shunichi Ikeda; Kentaro Tamaki, all of Sakai, Japan

[73] Assignee: Kyowa Hakko Kogyo Co., Ltd., Tokyo, Japan

[21] Appl. No.: 186,964

[22] Filed: Apr. 27, 1988

Related U.S. Application Data

[62] Division of Ser. No. 103,305, Oct. 1, 1987, Pat. No. 4,795,831, which is a division of Ser. No. 834,945, Feb. 28, 1986, Pat. No. 4,716,241.

[30] Foreign Application Priority Data

Mar. 1, 1985 [JP] Japan .................................. 60-40946
Jul. 5, 1985 [JP] Japan ................................. 60-147821

[51] Int. Cl.$^4$ .................. C07D 303/04; C07C 69/145; C07C 43/305
[52] U.S. Cl. .................... 549/332; 560/231; 568/579; 568/591
[58] Field of Search ................ 560/231; 568/579, 591; 549/332

[56] References Cited

U.S. PATENT DOCUMENTS

| | | | |
|---|---|---|---|
| 3,166,600 | 1/1965 | Lorette et al. .................. | 568/591 |
| 3,627,815 | 12/1971 | Hall, Jr. ......................... | 558/432 X |
| 4,571,308 | 2/1986 | Zanno et al. .................... | 530/801 X |
| 4,571,345 | 2/1986 | Verlander et al. ............... | 426/548 |
| 4,572,799 | 2/1986 | Zanno et al. .................... | 530/801 X |
| 4,622,417 | 11/1986 | Barnett et al. .................. | 530/801 X |
| 4,622,418 | 11/1986 | Barnett et al. .................. | 530/801 X |

FOREIGN PATENT DOCUMENTS 0128654 12/1984 European Pat. Off. .

OTHER PUBLICATIONS

Huguet, et al.; Helv. Chim. Acta, 65, (1982), pp. 2413–2421.

Primary Examiner—Joseph Paul Brust
Attorney, Agent, or Firm—Fitzpatrick, Cella, Harper & Scinto

[57] ABSTRACT

Novel cyclopentane derivatives which are useful as an intermediate for the preparation of N-(L-aspartyl)-N'-(2,2,5,5-tetramethylcyclopentanecarbonyl)-R-1,1-diaminoethane are represented by the formula (I)

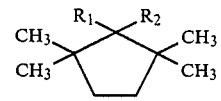

wherein $R_1$ is hydrogen and $R_2$ is cyano, formyl, carbamoyl, alkanesulfonyloxy, or

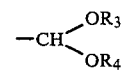

wherein $R_3$ and $R_4$ are the same or different and represent alkyl, substituted alkyl or $R_1$ and $R_2$ are combined to be methylsulfinylmethylene, acetoxymethylthiomethylene, halomethylthiomethylene, methylthiomethylene, alkoxymethylene, or —$CH_2$—O—.

3 Claims, No Drawings

CYCLOPENTANE DERIVATIVES

This application is a division of Ser. No. 103,305, filed 10/1/87, now U.S. Pat. No. 4,795,831, which is a division of Ser. No. 834,945, filed 2/28/86, now U.S. Pat. No. 4,716,241.

BACKGROUND OF THE INVENTION

The present invention relates to an intermediate for the preparation of N-(L-aspartyl)-N'-(2,2,5,5-tetramethylcyclopentanecarbonyl)-R-1,1-diaminoethane (hereinafter referred to as "gem-sweetener") represented by the formula:

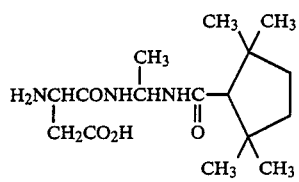

The gem-sweetener is a known compound which is disclosed in European patent application No. 128654A. The compound possesses a high degree of sweetness, without undesirable flavor notes and also possesses a high degree of stability in all types of aqueous systems and even upon cooking.

It is known that the compound is prepared by the steps shown in the following scheme.

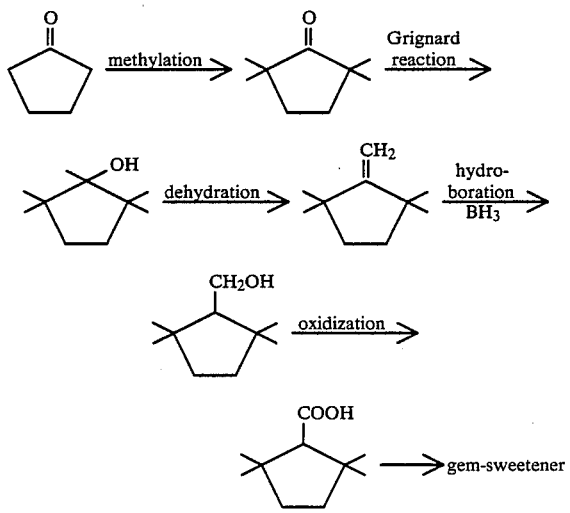

This method involves dangerous reactions, that is, Grignard reaction and hydroboration, and boron hydride which is used in the step of hydroboration is very expensive. Further, the total yield is only about 8% which is very low.

As the result of studies on an industrially advantageous process for the preparation of gem-sweetener, it has been found that 2,2,5,5-tetramethylcyclopentane carboxylic acid which is an intermediate for the preparation of gem-sweetener can be prepared without the above-described disadvantages of the known methods.

SUMMARY OF THE INVENTION

In accordance with the present invention, there is provided a novel compound which is useful as an intermediate for the preparation of gem-sweetener and which is represented by the formula (I):

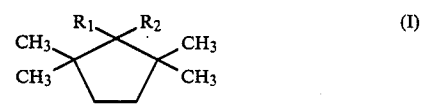

wherein $R_1$ is hydrogen and $R_2$ is cyano, formyl, carbamoyl, alkanesulfonyloxy, or

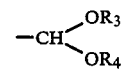

wherein $R_3$ and $R_4$ are the same or different and are alkyl, substituted alkyl or $R_1$ and $R_2$ are combined to be methylsulfinylmethylene, acetoxymethylthiomethylene, halomethylthiomethylene, methylthiomethylene, alkoxymethylene, or —$CH_2$—O—.

DESCRIPTION OF THE INVENTION

In the definitions of the individual groups in formula (I), the alkyl or alkyl moiety of alkanesulfonyloxy and alkoxymethylene includes straight or branched alkyl having 1 to 6 carbon atoms such as methyl, ethyl, propyl, butyl, etc.

The substituents of substituted alkyl include alkoxy, hydroxy and halogen. The definition of alkyl moiety of alkoxy is the same as that described above.

The halo group of halomethylthiomethylene and halogen include chloro, bromo, etc. The following is a general scheme for the production of the desired intermediates of the present invention:

In the scheme, each symbol has the following meaning.

| | |
|---|---|
| P-1 ... P-18: | Process |
| R' and R": | Alkyl |
| $R_3$ and $R_4$: | Having the same meaning as described above in the definition of the formula (I). |
| $A_c$: | Acetyl |
| X: | Halogen |
| ⌗ : | tetramethylcyclopentane |

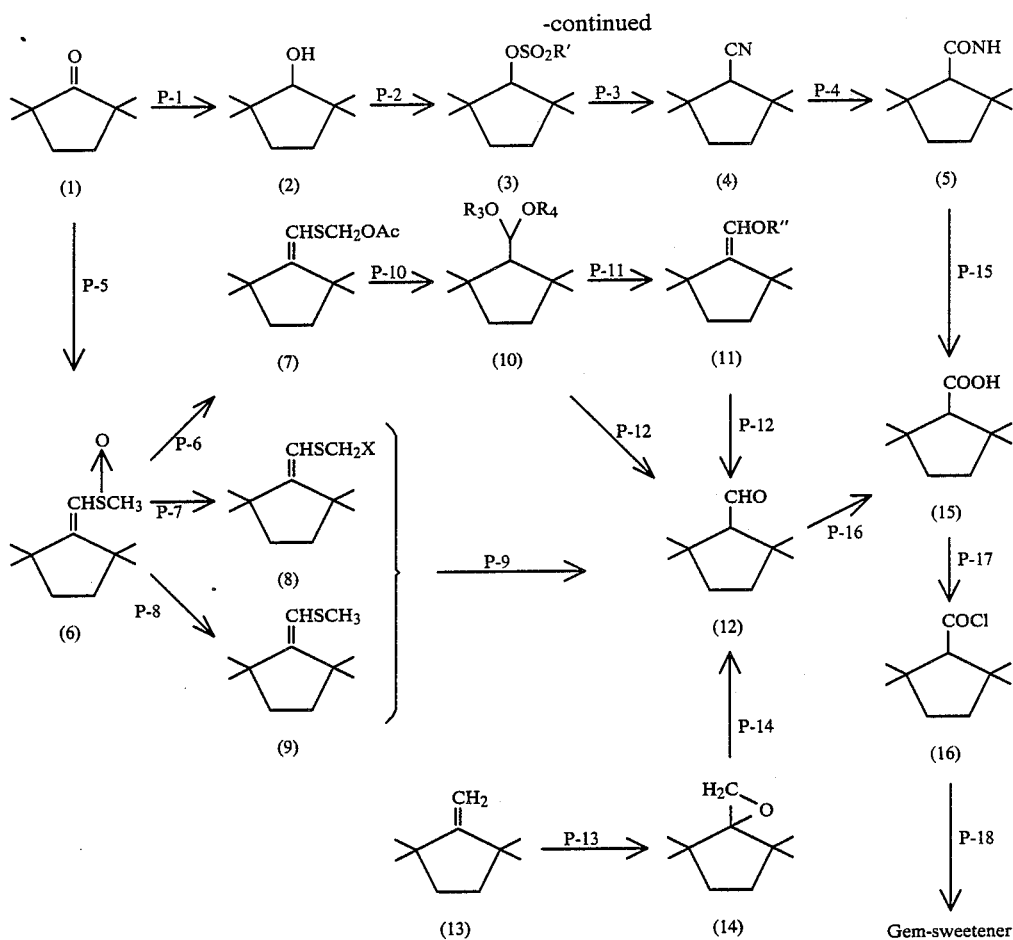

-continued

PROCESS 1

Compound 1, i.e. 2,2,5,5-tetramethylcyclopentanone is reduced in an inert solvent in the presence of a catalyst such as Raney nickel or a reducing agent such as sodium borohydride to provide Compound 2, i.e. 2,2,5,5-tetramethylcyclopentanol. The reduction is carried out at a temperature ranging from the room temperature to 180° C. for 3 to 30 hours. As the solvent, water, methanol, ethanol, dioxane, tetrahydrofuran, etc. may be used alone or in combination.

Compound 1 is a known compound which can be readily prepared from cyclopentanone, as shown in Reference Example 1.

PROCESS 2

Compound 2 is allowed to react with an alkanesulfonyl chloride in the presence of a base in an inert solvent to provide Compound 3, that is, 1-alkanesulfonyloxy-2,2,5,5-tetramethylcyclopentane. As the inert solvent, halogenated lower alkanes, for example, methylene chloride etc. are used. As the base, pyridine, triethylamine, etc. are used. The reaction is carried out at 0° to 100° C. for 1 to 40 hours.

PROCESS 3

Compound 3 is allowed to react with sodium cyanide in the presence of dimethylsulfoxide in a sealed tube at 150° to 300° C. for 5 to 30 hours to obtain Compound 4, that is, 1-cyano-2,2,5,5-tetramethylcyclopentane.

PROCESS 4

Compound 4 is subjected to hydrolysis in an aqueous solution of alkali hydroxides, for example, sodium hydroxide and potassium hydroxide to obtain Compound 5, that is, (2,2,5,5-tetramethylpentane-1-yl) carboxamide. The reaction is carried out at 0° to 110° C. for 1 to 30 hours.

PROCESS 5

Compound 1 is dissolved in an inert solvent, for example, dioxane, tetrahydrofuran, etc., and sodium hydride is added to the solution. After the solution is heated to 70° to 100° C., dimethylsulfoxide is added to the solution and the mixture is subjected to reaction with heating under reflux usually for 2 to 5 hours to provide Compound 6, i.e. 2,2,5,5-tetramethylcyclopentylidenemethyl methyl sulfoxide.

PROCESS 6

Compound 6 is allowed to react with acetic anhydride in the presence of a base in an inert solvent to provide Compound 7, i.e. 2,2,5,5-tetramethylcyclopentylidenemethyl acetoxymethyl sulfide. As the inert solvent, ethylene dichloride, chloroform, etc. are used and as the base, pyridine, etc. are used.

Pyridine can be used to serve as the solvent as well. The reaction is carried out at a temperature ranging from room temperature to 120° C. for 3 to 20 hours.

PROCESS 7

Compound 6 is allowed to react with acetyl halide, if necessary, in an inert solvent to provide Compound 8, i.e. 2,2,5,5-tetramethylcyclopentylidenemethyl halomethyl sulfide. As the inert solvent, methylene chloride, chloroform, tetrahydrofuran, etc. are used. As the acetyl halide, acetyl chloride, etc. are used in an amount more than the equivalent amount of Compound 6. The reaction is carried out at 0° to 120° C. for 1 to 30 hours.

PROCESS 8

Compound 6 is reduced in the presence of a reducing agent such as lithium aluminum hydride, if necessary, in an inert solvent to provide Compound 9, i.e. 2,2,5,5-tetramethylcyclopentylidenemethyl methylsulfide. As the inert solvent, tetrahydrofuran, dioxane, etc. are used. The reaction is carried out at around the room temperature for about 10 hours.

PROCESS 9

Compound 7, 8 or 9 is subjected to reaction with a lower alkanol in the presence of bromine under cooling to provide Compound 10, i.e. 1-formyl-2,2,5,5-tetramethylcyclopentane. The reaction is carried out at a temperature of from −30° to 80° C., preferably from −20° to 30° C. for 0.5 to 10 hours. The lower alkanol includes methanol, ethanol, etc.

PROCESS 10

Compound 7 which can be obtained according to Process 6 is subjected to reaction with an alkanol or a substituted alkanol in the presence of a halogenating agent in an inert solvent to provide Compound 10. The alkanol includes alkanols having 1 to 10 carbon atoms such as methanol, ethanol, propanol, etc. The substituent of the substituted alkanol includes lower alkoxy, hydroxy and halogen.

The halogenating agent includes chlorine, bromine, iodine, N-bromosuccinimide, etc, but bromine is preferable. The inert solvent includes halogenated lower alkanes such as chloroform, methylene chloride, etc., and ethers such as tetrahydrofuran, diethylether, etc.

A large excess (usually 50 to 500 equivalent weight) of alkanols is used on the basis of Compound 7 so as to serve also as a solvent. Usually 1 to 5 equivalent weight, preferably 3 to 3.5 equivalent weight, of the halogenating agent is used on the basis of Compound 7. The reaction is carried out at a temperature of −78° to 50° C. and is completed usually within 20 to 100 hours.

PROCESS 11

Compound 10 is subjected to incubation under basic conditions, for example, in the presence of 0.1 to 20 equivalent weight of a base such as sodium hydroxide and potassium hydroxide, in an inert solvent to provide Compound 11. The incubation of Compound 10 may be carried out using the reaction mixture obtained in Process 10 without isolating Compound 10. The inert solvent includes water, methanol, ethanol, dioxane, tetrahydrofuran and their mixture. The reaction is carried out usually at a temperature ranging from room temperature to 100° C. for 1 to 30 hours.

PROCESS 12

Compound 10 or Compound 11 is subjected to acid hydrolysis to provide Compound 12, i.e., 1-formyl-2,2,5,5-tetramethylcyclopentane.

The reaction is carried out in an inert solvent such as tetrahydrofuran in the presence of acid such as hydrochloride at room temperature for 1 to 10 hours.

PROCESS 13

Compound 13, i.e. 1-methylene-2,2,5,5-tetramethylcyclopentane, is oxidized by a peroxidizing agent such as m-chloroperbenzoic acid (MCPBA), if necessary, in an inert solvent to provide Compound 14, i.e. 1-methylene-2,2,5,5-tetramethylcyclopentane oxide. As the inert solvent, acetonitrile, tetrahydrofuran, methanol, etc. are used. The reaction temperature depends on the oxidizing agent. It may be around the room temperature when m-chloroperbenzoic acid is used, where the reaction completes in 1 to 10 hours. Compound 13 is a known compound which can be prepared according to the procedure shown in Reference Example 3.

PROCESS 14

Compound 14 is treated with a solution of a Lewis acid in an appropriate solvent, for example, ether to provide Compound 12. The Lewis acid includes boron trifluoride ($BF_3$), magnesium bromide, etc. An appropriate amount of the Lewis acid to be used is usually 1 to 10% (W/W) on the basis of the substrate. The reaction is carried out at 0° to 100° C. for 0.5 to 10 hours.

Processes P-15 to P-18 mentioned in the above scheme are known processes and are described later in Reference Examples.

In the Processes described above, the purification and isolation of the desired compounds are carried out according to the known methods. When the desired compound is in the form of an oily substance at room temperature, the compound is purified by rectification. When the compound is in a solid form at room temperature, the compound is purified by concentration, extraction, crystallization, etc.

Certain specific embodiments of the invention are illustrated by the following representative examples.

EXAMPLE 1

P-1 and P-2

(1) 54.9 g of 2,2,5,5-tetramethylcyclopentanone was dissolved in a solvent mixture of 95 ml of methanol and 95 ml of water, and 24.0 g of sodium borohydride was added thereto. The mixture was stirred at 70° C. for 15 hours. The reaction solution was concentrated under reduced pressure, and 100 ml of water was added thereto. The mixture was twice extracted with 100 ml of chloroform, and the organic layers were combined and washed with 100 ml of an aqueous saturated sodium chloride solution. Then, the solution was concentrated under reduced pressure. The liquid residue was distilled under reduced pressure, whereby 43.25 g of 2,2,5,5-tetramethylcyclopentanol was obtained as a colorless oily substance (b.p. 40° C./3 mmHg).

---

IR $\nu_{OH}$ 3450 cm$^{-1}$
$^1$H—NMR (90 MHz in $CDCl_3$); δ
  0.93(s, 6H), 1.04(s, 6H), 1.25(m, 4H), 3.24(s, 1H)
Elemental analysis as $C_9H_{18}O$
  Calculated:   C 75.99%   H 12.76%
  Found:        C 75.88%   H 12.67%

---

(2) 2.84 g of 2,2,5,5-tetramethylcyclopentanol and 3.2 ml of pyridine were dissolved in 20 ml of methylene chloride, and 4.5 g of methanesulfonyl chloride was added thereto. The mixture was stirred at room temperature for 12 hours, and then 50 ml of aqueous saturated sodium hydrogen carbonate solution was added thereto. The mixture was extracted with 50 ml of ethyl acetate, and the organic layer was washed with aqueous 10% copper sulfate solution, and concentrated under reduced pressure. The resulting residue was recrystallized from n-hexane, whereby 1.26 g of 1-methanesulfonyloxy-2,2,5,5-tetramethylcyclopentane was obtained (m.p. 46° C.).

$^1$H—NMR (90 MHz in CDCl$_3$); δ
    1.03(s, 6H), 1.13(s, 6H), 1.56(m, 4H), 3.03(s, 3H), 4.26(s, 1H)
IR (KBr) 1170, 1350 cm$^{-1}$
Elemental analysis as C$_{10}$H$_{20}$O$_3$S
    Calculated:    C 54.51%    H 9.15%
    Found:         C 54.28%    H 9.11%

EXAMPLE 2

P-3

20 ml of dimethylsulfoxide was added to 1.10 g of 1-methanesulfonyloxy-2,2,5,5-tetramethylcyclopentane and 980 mg of sodium cyanide, and the mixture was stirred with heating at 200° C. for 20 hours in a sealed tube.

After cooling, 200 ml of water was added thereto, and the mixture was extracted with 300 ml of ethyl acetate. The organic layer was washed with 200 ml of water, and concentrated under reduced pressure. The thus obtained oily substance was subjected to silica gel column chromatography using ethyl acetate-n-hexane as an eluent, whereby 340 mg of 1-cyano-2,2,5,5-tetramethylcyclopentane was obtained (b.p. 106° C./35 mmHg).

$^1$H—NMR (90 MHz in CDCl$_3$); δ
    1.19(s, 6H), 1.25(s, 6H), 1.67(m, 4H), 2.34(s, 1H)
IR (neat) 2200 cm$^{-1}$
Elemental analysis as C$_{10}$H$_{17}$N
    Calculated:    C 79.41%    H 11.33%
    Found:         C 79.40%    H 11.35%

EXAMPLE 3

P-4

760 mg of 1-cyano-2,2,5,5-tetramethylcyclopentane was dissolved in 5 ml of aqueous 3N sodium hydroxide solution and 10 ml of MeOH, and the solution was stirred at room temperature for 10 hours. Then, 10 ml of water was added thereto, and the mixture was twice extracted with 30 ml of chloroform. The organic layers were combined, washed with 50 ml of water and concentrated under reduced pressure. The thus obtained residue was recrystallized from n-hexane, whereby 640 mg of (2,2,5,5-tetramethylcyclopentane-1-yl) carboxamide was obtained (m.p. 97.7° C.).

$^1$H—NMR (90 MHz in CDCl$_3$); δ
    1.11(s, 6H), 1.14(s, 6H), 1.55(m, 4H), 1.92(s, 1H), 5.40(s, 1H), 5.76(s, 1H)
Elemental analysis as C$_{10}$H$_{19}$ON
    Calculated:    C 70.96%,   H 11.32%,   N 8.28%
    Found:         C 70.79%,   H 11.32%,   N 8.29%

EXAMPLE 4

P-5

28.0 g of 2,2,5,5-tetramethylcyclopentanone was dissolved in 50 ml of tetrahydrofuran, and 9.8 g of 50% sodium hydride was added thereto. The mixture was heated under reflux.

A mixed solution of 40 ml of dimethylsulfoxide and 50 ml of tetrahydrofuran was slowly added dropwise at the same temperature. The mixture was further heated at the same temperature for 3 hours, and cooled. Then, 200 ml of water was added thereto, and the mixture was twice extracted with 200 ml of ethyl acetate. The organic layers were washed with an aqueous saturated sodium chloride solution, dried over anhydrous magnesium sulfate, and filtered. The filtrate was concentrated under reduced pressure, and the residue was crystallized from 70 ml of n-hexane, whereby 29.2 g of 2,2,5,5-tetramethylcyclopentylidenemethyl methyl sulfoxide was obtained (m.p. 74.7° C.).

$^1$H—NMR (90 MHz in CDCl$_3$); δ
    1.09(s, 3H), 1.15(s, 3H), 1.23(s, 3H), 1.43(s, 3H), 1.62(s, 4H), 2.57(s, 3H), 5.90(s, 1H)
IR $\nu_{S=O}$ 1050 cm$^{-1}$
Elemental analysis as C$_{11}$H$_{20}$OS
    Calculated:    C 65.95%    H 10.06%
    Found:         C 65.76%    H 10.00%

EXAMPLE 5

P-6

5.0 g of 2,2,5,5-tetramethylcyclopentylidenemethyl methyl sulfoxide, 5.2 g of acetic anhydride, 3.5 g of pyridine and 5 ml of 1,2-dichloroethane were mixed, and heated under reflux for 7.5 hours. After cooling, 50 ml of aqueous saturated sodium hydrogen carbonate solution was added thereto, and the mixture was extracted with 200 ml of ethyl acetate. The organic layer was washed with 80 ml of aqueous 10% copper sulfate solution and again with 80 ml of water.

The organic layer was dried over anhydrous magnesium sulfate and concentrated under reduced pressure. The liquid residue was subjected to silica gel column chromatography using ethyl acetate-n-hexane as an eluent and then distilled under reduced pressure, whereby 5.2 g of 2,2,5,5-tetramethylcyclopentylidenemethyl acetoxymethyl sulfide was obtained as a colorless oily substance (b.p. 81° C./2 mmHg).

IR $\nu_{C=O}$ 1750 cm$^{-1}$
$^1$H—NMR (90 MHz in CDCl$_3$); δ
    1.07(s, 6H), 1.24(s, 6H), 1.56(s, 4H), 2.08(s, 3H), 5.17(s, 2H), 5.75(s, 1H)
Elemental analysis as C$_{13}$H$_{20}$O$_2$S
    Calculated:    C 64.96%    H 8.39%
    Found:         C 64.83%    H 8.27%

EXAMPLE 6

P-7

1.0 g of 2,2,5,5-tetramethylcyclopentylidenemethyl methyl sulfoxide was dissolved in 10 ml of methylene chloride, and 470 mg of acetyl chloride was added dropwise. The mixture was subjected to reaction at room temperature for 12 hours, and then 50 ml of 5% sodium hydrogen carbonate was added thereto. The mixture was extracted twice with 50 ml of chloroform, and the organic layers were dried over anhydrous magnesium sulfate and filtered. The filtrate was concentrated under reduced pressure, whereby 960 mg of 2,2,5,5-tetramethylcyclopentylidenemethyl chloromethyl sulfide was obtained.

$^1$H—NMR (90 MHz in CDCl$_3$); δ
  1.09(s, 6H), 1.24(s, 6H), 1.57(s, 4H), 4.73(s, 2H), 5.71(s, 1H)
Elemental analysis as C$_{11}$H$_{19}$SCl
  Calculated:   C 60.39%    H 8.75%
  Found:        C 60.43%    H 8.81%

EXAMPLE 7

P-8

20 g of 2,2,5,5-tetramethylcyclopentylidenemethyl methyl sulfoxide was dissolved in 200 ml of tetrahydrofuran, and 4.0 g of lithium aluminum hydride was added thereto in small portions. The mixture was stirred at room temperature for 10 hours, and then 100 ml of ethyl acetate was added dropwise thereto. After the mixture was subjected to filtration, the filtrate was concentrated under reduced pressure. The oily substance was subjected to silica gel column chromatography using ethyl acetate-n-hexane as an eluent, whereby 13.8 g of 2,2,5,5-tetramethylcyclopentylidenemethyl methyl sulfide was obtained as an oily substance.

$^1$H—NMR (90 MHz in CDCl$_3$); δ
  1.04(s, 6H), 1.24(s, 6H), 1.55(s, 4H), 2.22(s, 3H), 5.48(s, 1H)
Elemental analysis as C$_{11}$H$_{20}$S
  Calculated:   C 71.67%    H 10.94%
  Found:        C 71.51%    H 10.72%

EXAMPLE 8

P-9

4.5 mg of 2,2,5,5-tetramethylcyclopentylidenemethyl acetoxymethyl sulfide was dissolved in 90 ml of methanol, and the solution was cooled to −50° C. 8.63 g of bromine was added thereto at the same temperature, and the mixture was warmed gradually up to room temperature.

After stirring at room temperature for 8 hours, 300 ml of water was added thereto, and the mixture was extracted twice with 200 ml of chloroform. The organic layers were combined, washed with 300 ml of aqueous saturated sodium hydrogen carbonate solution and dried over anhydrous magnesium sulfate. The solvent was evaporated under reduced pressure. The liquid residue was distilled under reduced pressure, whereby 2.47 g of 1-formyl-2,2,5,5-tetramethylcyclopentane was obtained as a colorless oily substance (b.p. 102° C./45 mmHg).

$^1$H—NMR (90 MHz in CDCl$_3$); δ
  1.10(s, 6H), 1.19(s, 6H), 1.62(s, 4H), 1.91(d, J = 5.4 Hz, 1H), 9.77(d, J = 5.4 Hz, 1H)
IR ν$_{C=O}$ 1710 cm$^{-1}$ (neat)
Elemental analysis as C$_{10}$H$_{18}$O
  Calculated:   C 77.86%    H 11.76%
  Found:        C 77.83%    H 11.77%

EXAMPLE 9

P-10

96.8 g of 2,2,5,5-tetramethylcyclopentylidenemethyl acetoxymethyl sulfide was dissolved in 1.6 l of methanol, and the solution was cooled to −50° C. Then, a solution of 204.8 g of bromine in 400 ml of chloroform was added dropwise thereto at the same temperature, and the mixture was stirred for one hour. After further stirring at room temperature for 24 hours, the reaction mixture was added dropwise to 1.6 l of aqueous 2N sodium hydroxide solution with ice cooling. The mixture was extracted twice with 500 ml of chloroform, and the organic layers were combined and dried over anhydrous magnesium sulfate. The solvent was evaporated under reduced pressure.

The residue was distilled under reduced pressure, whereby 57.6 g of 1-formyl-2,2,5,5-tetramethylcyclopentanedimethyl acetal was obtained as an oily substance.

Yield: 72%, (b.p. 49–52° C./0.4 mmHg)
$^1$H—NMR (90 MHz in CDCl$_3$); δ
  0.96(s, 6H), 1.04(s, 6H), 1.43(s, 4H), 1.45(d, J = 9 Hz, 1H), 3.27(s, 2H), 4.37(d, J = 9 Hz, 1H)
Elemental analysis as C$_{12}$H$_{24}$O$_2$
  Calculated:   C 71.95%    H 12.08%
  Found:        C 72.22%    H 12.30%

EXAMPLE 10

P-11

10.0 g of 1-formyl-2,2,5,5-tetramethylcyclopentanedimethyl acetal was dissolved in 20 ml of methanol and 10 ml of aqueous 1N sodium hydroxide solution, and the solution was heated under reflux for 2 hours. After the reaction, the reaction mixture was cooled, and extracted twice with 100 ml of chloroform. The organic layers were combined, and dried over anhydrous magnesium sulfate. The solvent was evaporated under reduced pressure. The residue was distilled under reduced pressure, whereby 4.45 g of 2,2,5,5-tetramethylcyclopentylidenemethyl methyl ether was obtained as an oily substance. Yield: 53%. (b.p. 40°–42° C./0.1 mmHg).

$^1$H—NMR (90 MHz in CDCl$_3$); δ
  1.02(s, 6H), 1.17(s, 6H), 1.49(s, 4H), 3.45(s, 3H), 5.63(s, 1H)
Elemental analysis as C$_{11}$H$_{20}$O
  Calculated:   C 78.51%    H 11.98%
  Found:        C 78.79%    H 12.19%

EXAMPLE 11

P-12

20.0 g of 1-formyl-2,2,5,5-tetramethylcyclopentane dimethylacetal was dissolved in 200 ml of tetrahydrofuran, and 100 ml of 1N hydrochloric acid was added thereto. The mixture was vigorously stirred at room temperature for 3 hours, and 400 ml of water was added thereto. The mixture was extracted twice with 400 ml of ethyl acetate. The organic layers were combined, washed with 1 l of water and then with 1 l of aqueous saturated sodium chloride solution, and dried over anhydrous sodium sulfate.

After filtration, the solvent was evaporated under reduced pressure, and the residue was distilled under reduced pressure, whereby 13.6 g of 1-formyl-2,2,5,5-tetramethylcyclopentane was obtained as a colorless oily substance. Yield 88%. (b.p. 102° C./45 mmHg).

$^1$H—NMR (90 MHz in CDCl$_3$); δ
1.10(s, 6H), 1.19(s, 6H), 1.62(s, 4H), 1.91(d, J = 5.4 Hz, 1H), 9.77(d, J = 5.4 Hz, 1H)
IR $\nu_{C=O}^{neat}$ 1710 cm$^{-1}$
Elemental analysis as C$_{10}$H$_{18}$O

| | | |
|---|---|---|
| Calculated: | C 77.86% | H 11.76% |
| Found: | C 77.83% | H 11.77% |

EXAMPLE 12

P-12

10 g of 2,2,5,5-tetramethylcyclopentylidenemethyl methyl ether was dissolved in 100 ml of tetrahydrofuran, and 50 ml of 6N-hydrochloric acid was added thereto. The mixture was vigorously stirred at room temperature for 3 hours, and then treated in the same manner as in Example 11 to obtain 8.60 g of 1-formyl-2,2,5,5-tetramethylcyclopentane. Yield 94%.

EXAMPLE 13

P-13

43.44 g of 1-methylene-2,2,5,5-tetramethylcyclopentane was dissolved in 600 ml of acetonitrile, and 147.9 g of m-chloroperbenzoic acid was added thereto in small portions with ice cooling. After stirring at room temperature for 7 hours, 480 ml of aqueous 10% sodium thiosulfate solution and 500 ml of aqueous saturated sodium hydrogen carbonate solution were added thereto, and the precipitate was removed by filtration. The filtrate was extracted twice with 500 ml of ethyl acetate, and the organic layers were combined. The solvent was evaporated under reduced pressure. The residue was distilled under reduced pressure, whereby 42.04 g of 1-methylene-2,2,5,5-tetramethylcyclopentane oxide was obtained as an oily substance (b.p. 54° C./15 mmHg).

$^1$H—NMR (90 MHz in CDCl$_3$); δ
0.87(s, 6H), 1.01(s, 6H), 1.65(s, 4H), 2.63(s, 2H)
Elemental analysis as C$_{10}$H$_{18}$O

| | | |
|---|---|---|
| Calculated: | C 77.86% | H 11.76% |
| Found: | C 77.65% | H 11.78% |

EXAMPLE 14

P-14

3.08 g of 1-methylene-2,2,5,5-tetramethylcyclopentane oxide was dissolved in 40 ml of ethyl acetate, and the solution was cooled to −50° C. Then, 0.14 g of boron tetrafluoride-ether complex was added thereto, and the mixture was stirred at room temperature for one hour. Then, 50 ml of aqueous saturated sodium hydrogen carbonate solution was added thereto, and the resulting two layers were separated. The organic layer was concentrated under reduced pressure, and distilled under reduced pressure, whereby 2.68 g of 1-formyl-2,2,5,5-tetramethylcyclopentane was obtained as an oily substance (b.p. 102° C./45 mmHg).

IR $\nu_{C=O}$ 1710 cm$^{-1}$ (neat)
$^1$H—NMR (90 MHz in CDCl$_3$); δ
1.10(s, 6H), 1.19(s, 6H), 1.62(s, 4H), 1.91(d, J = 5.4 Hz, 1H), 9.77(d, J = 5.4 Hz, 1H)
Elemental analysis as C$_{10}$H$_{18}$O

| | | |
|---|---|---|
| Calculated: | C 77.86% | H 11.76% |
| Found: | C 77.83% | H 11.77% |

REFERENCE EXAMPLE 1

Preparation of 2,2,5,5-tetramethylcyclopentanone 1.5 l of tetrahydrofuran was added to 144 g of 50% sodium hydride and a solution of 53.6 g of cyclopentanone in 350 ml of terahydrofuran was added dropwise thereto with ice cooling in a nitrogen gas stream. Then, a solution of 285 ml of dimethy sulfate and 120 ml of tetrahydrofuran was slowly added dropwise thereto with ice cooling, and the mixture was heated under reflux for 2 hours.

After cooling, 100 ml of t-butanol was slowly added dropwise thereto to decompose excess sodium hydride, and then 1.0 l of water was added thereto. The reaction mixture was further heated for 2 hours under reflux to decompose excess dimethyl sulfate. After cooling, the resulting two layers were separated and the organic layer was washed with aqueous saturated sodium chloride solution, and dried over anhydrous sodium sulfate. The solvent was distilled away under reduced pressure, and the residue was distilled under reduced pressure, whereby 59 g of 2,2,5,5-tetramethylcyclopentanone was obtained (b.p. 55° C./20 mmHg).

$^1$H—NMR (90 MHz in CDCl$_3$); δ
1.04(s, 12H), 1.77(s, 4H)
IR $\nu_{C=O}$ 1734 cm$^{-1}$ (neat)

REFERENCE EXAMPLE 2

Preparation of 1,2,2,5,5-pentamethylcyclopentanol 100 ml of a 3M methylmagnesium bromide/ether solution was added to a solution of 30 g of 2,2,5,5-tetramethylcyclopentanone in 50 ml of ether under a nitrogen gas atmosphere, and the mixture was stirred at room temperature overnight. Then, 65 ml of aqueous saturated ammonium chloride solution was added dropwise thereto and the mixture was stirred for 10 minutes. The ether layer was subjected to decantation and the residue was extracted with ether. The ether layers were dried over anhydrous sodium sulfate, and concentrated under reduced pressure, whereby 30 g of 1,2,2,5,5-pentamethylcyclopentanol was obtained.

$^1$H-NMR (90 MHz in CDCl$_3$); δ; 1.00(s, 12H), 1.03(s, 3H), 1.55(m, 4H).
IR $\nu_{O-H}$ 3480 cm$^{-1}$ (neat).

REFERENCE EXAMPLE 3

Preparation of 1-methylene-2,2,5,5-tetramethylcyclopentane 30 g of 1,2,2,5,5-pentamethylcyclopentanol was dissolved in 150 ml of pyridine, and 20 ml of thionyl chloride was added dropwise thereto with ice cooling. The reaction mixture was stirred overnight and subjected to filtration. Ether and water were added to the filtrate, and the resulting layers were separated. The organic layer was washed twice with 200 ml of water, and then dried over anhydrous sodium sulfate. The solvent was distilled away under reduced pressure, whereby 10.8 g of 1-methylene-2,2,5,5-tetramethylcyclopentane was obtained (b.p. 137°–140° C./760 mmHg).

$^1$H-NMR (90 MHz in CDCl$_3$); δ;
1.10(s, 12H), 1.76(s, 4H), 4.76(s, 2H).

REFERENCE EXAMPLE 4

Preparation of 2,2,5,5-tetramethylcyclopentanecarboxylic acid 3.38 g of (2,2,5,5-tetramethylcyclopentane-1-yl) carboxamide was dissolved in 30 ml of methanol, and 15 ml of an aqueous 3N sodium hydroxide solution was added thereto. Then, the mixture was heated at 80° C. for 5 hours. After cooling, 40 ml of 2N hydrochloric acid was added thereto, and the mixture was extracted with 100 ml and 50 ml of ethyl acetate. The organic layers were combined, washed with 100 ml of water and 50 ml of aqueous saturated sodium chloride solution, and then dried over anhydrous magnesium sulfate. After removal of magnesium sulfate by filtration, the filtrate was concentrated under reduced pressure, whereby 3.20 g of 2,2,5,5-tetramethylcyclopentanecarboxylic acid was obtained. Yield 94%. (m.p. 113.6° C.).

IR $\nu_{max}^{KBr}$ cm$^{-1}$ 2930, 1693
$^1$H—NMR (90 MHz in CDCl$_3$); δ
1.11(s, 12H), 1.53(s, 4H), 2.19(s, 1H)

REFERENCE EXAMPLE 5

Preparation of 2,2,5,5-tetramethylcyclopentanecarboxylic acid 2.47 g of 1-formyl-2,2,5,5-tetramethylcyclopentane was dissolved in 26 ml of acetone, and 5.2 ml of Jones' reagent was added thereto with ice cooling. After stirring at room temperature for 4 hours, 26 ml of water, 26 ml of ethyl acetate and 2.6 ml of isopropyl alcohol were added thereto, and the mixture was stirred at room temperature for 30 minutes, and the resulting layers were separated. The organic layer was washed with water and aqueous saturated sodium chloride solution, dried over anhydrous magnesium sulfate, and subjected to filtration. The filtrate was concentrated under reduced pressure, whereby 2.51 g of 2,2,5,5-tetramethylcyclopentanecarboxylic acid was obtained. Yield 92%.

REFERENCE EXAMPLE 6

Preparation of ultimate sweetening compound 2.51 g of 2,2,5,5-tetramethylcyclopentanecarboxylic acid was dissolved in 10 ml of toluene, and 2.5 ml of thionyl chloride was added thereto. The mixture was stirred at 80° C. for 3 hours. The reaction solution was concentrated and then distilled under reduced pressure, whereby 2.0 g of 2,2,5,5-tetramethylcyclopentanecarbonyl chloride was obtained. Yield 69%. (b.p. 110°–120° C./60 mmHg).

REFERENCE EXAMPLE 7

(1) 50 g of L-alanine methyl ester hydrochloride was dissolved in a solvent mixture of 357 ml of N,N-dimethylformamide and 357 ml of tetrahydrofuran, and the mixture was cooled to −50° C. Then, a solution of 72.3 g of triethylamine in 179 ml of tetrahydrofuran was added thereto at the same temperature, and a solution of 67.4 g of 2,2,5,5-tetramethylcyclopentanecarbonyl chloride in 179 ml of tetrahydrofuran was further added thereto at the same temperature.

The mixture was warmed to room temperature with stirring and the reaction was further carried out at room temperature for 90 minutes. After the reaction, 1.8 l of water was added thereto, and the mixture was extracted with ethyl acetate. The organic layer was washed with water and aqueous saturated sodium chloride solution, dried over anhydrous magnesium sulfate, and filtered. The filtrate was concentrated under reduced pressure, whereby 89.6 g of (−)-N-(2,2,5,5-tetramethylcyclopentanecarbonyl) alanine methyl ester was obtained as crystals. Yield 98.3%. (m.p. 86.7° C.).

$[\alpha]_D^{20}$ −58.0° (c = 0.2, MeOH)
$^1$H—NMR (90 MHz in CDCl$_3$); δ
1.10(s, 12H), 1.39(d, J = 8 Hz, 3H), 1.55(m, 4H),
1.86(s, 1H), 3.74(s, 3H), 4,69(quint. J = 8 Hz, 1H),
5.87(br.s, 1H)
IR$\nu_{max}^{KBr}$ cm$^{-1}$ 3300, 2920, 1760, 1650, 1540

(2) 87.6 g of (−)-N-(2,2,5,5-tetramethylcyclopentanecarbonyl) alanine methyl ester was dissolved in 700 ml of methanol, and an ammonia gas was blown therein till saturation with cooling. The reaction solution was kept in a closed vessel at room temperature for 20 hours.

Then, the mixture was concentrated under reduced pressure, whereby 82.8 g of (−)-N-(2,2,5,5-tetramethylcyclopentanecarbonyl) alanine amide was obtained as crystals. Yield 100%. (m.p. 155.4° C.).

$[\alpha]_D^{20}$ −41.2° (c = 0.2, MeOH)
$^1$H—NMR (90 MHz in CDCl$_3$); δ
1.05(s, 12H), 1.34(d, J = 8 Hz, 3H), 1.50(m, 4H),
1.88(s, 1H), 4.63(quint, J = 8 Hz, 1H)
IR $\nu_{max}^{KBr}$ cm$^{-1}$ 3370, 3190, 2920, 1680, 1650, 1620, 1500

(3) 6.00 g of (−)-N-(2,2,5,5-tetramethylcyclopentanecarbonyl) alanine amide was suspended in 20 ml of benzyl alcohol, and 9.16 g of iodobenzene diacetate was added thereto with ice cooling. The mixture was stirred at the same temperature for 3 hours, and further at room temperature for 3 hours. Then, 100 ml of aqueous saturated sodium hydrogen carbonate solution and 300 ml of chloroform were added thereto, and the resulting layers were separated. The organic layer was dried over anhydrous magnesium sulfate and filtered. The filtrate was concentrated under reduced pressure, and the residue was crystallized from 20 ml of toluene, whereby 6.70 g of (−)-N-(2,2,5,5-tetramethylcyclopentanecarbonyl)-N'-benzyloxycarbonyl-1,1-diaminoethane was obtained. Yield 77%. (m.p. 146.5° C.).

$[\alpha]_D^{20}$ −22° (c = 0.2, MeOH)
$^1$H—NMR (90 MHz in CDCl$_3$); δ
1.03(s, 9H), 1.06(s, 3H), 1.50(m, 7H), 1.74(s, 1H), 5.05(s, 2H), 5.18(q, J = 8 Hz, 1H), 7.30(s, 5H)
IR $\nu_{max}^{KBr}$ cm$^{-1}$ 3280, 2920, 1690, 1660, 1640, 1560, 1515

(4) 3.46 g of (−)-N-(2,2,5,5-tetramethylcyclopentanecarbonyl)-N'-benzyloxycarbonyl-1,1-diaminoethane was dissolved in 30 ml of tetrahydrofuran, and 1.20 g of acetic acid and 350 mg of 10% palladium-carbon catalyst were added thereto. The mixture was stirred at room temperature under the atmospheric pressure for 5 hours while blowing hydrogen therein. After the reaction, 1.01 g of triethylamine was added thereto, and the catalyst was removed by filtration. The filtrate was concentrated to about 10 ml under reduced pressure (solution A).

Separately, 3.57 g of $N^\alpha$-benzyloxycarbonyl-$\beta$-benzyl-L-aspartic acid was dissolved in a solvent mixture of 10 ml of tetrahydrofuran and 10 ml of N,N-dimethylformamide, and the solution was cooled to $-78°$ C. Then, a solution of 1.01 g of triethylamine in 3 ml of tetrahydrofuran and a solution of 1.37 g of isobutyl chloroformate in 3 ml of tetrahydrofuran were added thereto, and the mixture was stirred for one hour (solution B).

The solution A was added to the solution B at $-78°$ C., and the mixture was stirred at the same temperature for 30 minutes, and further at room temperature for one hour.

Then, 200 ml of water was added thereto, and the mixture was extracted with 350 ml of ethyl acetate. The organic layer was washed successively with 100 ml of aqueous 10% citric acid solution, 150 ml of aqueous saturated sodium hydrogen carbonate solution, and aqueous saturated sodium chloride solution, dried over anhydrous magnesium sulfate and filtered. The filtrate was concentrated under reduced pressure and purified by column chromatography on silica gel using chloroform as an eluent, whereby 3.30 g of N-($N^\alpha$-benzyloxycarbonyl-$\beta$-benzyl-L-aspartyl)-N'-(2,2,5,5-tetramethylcyclopentanecarbonyl)-R-1,1-diaminoethane was obtained as crystals. Yield 79%. (m.p. 115.7° C.).

$[\alpha]_D^{20}$ $-28.5°$ (c = 0.2, MeOH)
$^1$H—NMR (90 MHz in CDCl$_3$); $\delta$
1.04(s, 9H), 1.08(s, 1H), 1.44(d, J = 8 Hz, 3H),
2.84(ABdq. $J_{AB}$=18 Hz, $J_{AX}$=$J_{BX}$=6 Hz, 2H), 4.48(m, 1H), 5.06(s, 4H), 5.28(q, J = 8 Hz, 1H), 7.30(s, 10H)
IR $\nu_{max}^{KBr}$ cm$^{-1}$ 3350, 3290, 3240, 2920, 1740, 1710, 1650, 1540, 1510

(5) 5.52 g of N-($N^\alpha$-benzyloxycarbonyl-$\beta$-benzyl-L-aspartyl)-N'-(2,2,5,5-tetramethylcyclopentanecarbonyl)-R-1,1-diaminoethane was dissolved in a solvent mixture of 50 ml of methanol and 20 ml of water, and 1.1 g of 10% palladium-carbon catalyst was added thereto. Then, the mixture was subjected to catalytic reduction at the ordinary temperature under a hydrogen pressure of 15 kg/cm$^2$ for 5 hours. After the reaction, the catalyst was removed by filtration, and the filtrate was concentrated under reduced pressure. The residue was crystallized from 20 ml of water, whereby 2.26 g of N-L-aspartyl-N'-(2,2,5,5-tetramethylcyclopentanecarbonyl)-R-1,1-diaminoethane was obtained. Yield 69%.

$[\alpha]_D^{20}$ 19.7° (c = 1, H$_2$O)
$^1$H—NMR (90 MHz in DMSO—d$_6$); $\delta$
1.04(s, 12H), 1.24(d, J = 8 Hz, 3H), 1.48(m, 4H), 1.96(s, 1H), 3.70(m, 1H)
IR $\nu_{max}^{KBr}$ cm$^{-1}$ 3300, 1670, 1555, 1505

What is claimed is:

1. A compound represented by the formula

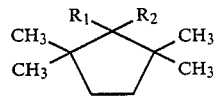

wherein R$_1$ is hydrogen and R$_2$ is

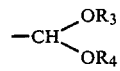

wherein R$_3$ and R$_4$ are the same or different and are straight or branched C$_{1-6}$ alkyl, straight or branched C$_{1-6}$ alkyl, substituted with 1 to 3 alkoxy, hydroxy, chloro or bromo substituents, or R$_1$ or R$_2$ are combined to be acetoxymethylthiomethylene, straight or branched C$_{1-6}$ alkoxymethylene, or —CH$_2$—O—.

2. A compound according to claim 1, wherein R$_1$ is hydrogen and R$_2$ is dimethyloxymethyl.

3. A compound according to claim 1, wherein R$_1$ and R$_2$ are combined and represent a member selected from the group consisting of acetoxymethylthiomethylene, methoxymethylene and —CH$_2$O—.

* * * * *

UNITED STATES PATENT AND TRADEMARK OFFICE
CERTIFICATE OF CORRECTION

PATENT NO. : 4,847,390
DATED : July 11, 1989
INVENTOR(S) : TAKAYOSHI YAMAUCHI, ET AL.

It is certified that error appears in the above-identified patent and that said Letters Patent is hereby corrected as shown below:

COLUMN 9

Line 42, "4.5 mg" should read --4.5 g--.

COLUMN 12

Line 17, "dimethy sulfate" should read --dimethyl sulfate--.

COLUMN 14

Line 18, "4,69" should read --4.69--.

COLUMN 16

Line 35, "$R_1$ or $R_2$" should read --$R_1$ and $R_2$--.

Signed and Sealed this

Fifth Day of June, 1990

Attest:

HARRY F. MANBECK, JR.

*Attesting Officer*     *Commissioner of Patents and Trademarks*